United States Patent [19]

Steiger

[11] Patent Number: 5,226,310

[45] Date of Patent: Jul. 13, 1993

[54] METHODS AND APPARATUSES FOR MEASUREMENT OF THE STRENGTHS, PORE PRESSURES, AND MECHANICAL PROPERTIES OF LOW PERMEABILITY GEOLOGIC MATERIALS

[75] Inventor: Ronald P. Steiger, Houston, Tex.

[73] Assignee: Exxon Production Research Company, Houston, Tex.

[21] Appl. No.: 577,326

[22] Filed: Aug. 31, 1990

[51] Int. Cl.$^5$ .................................... G01N 15/08
[52] U.S. Cl. .................................... 73/38; 73/794
[58] Field of Search .............. 73/38, 794, 795, 798, 73/153

[56] References Cited

U.S. PATENT DOCUMENTS

| | | | |
|---|---|---|---|
| 3,199,341 | 8/1965 | Heuer, Jr. et al. | 73/820 |
| 3,421,366 | 1/1969 | Ely | 73/819 |
| 3,423,994 | 1/1969 | Scott et al. | 73/819 |
| 3,423,995 | 1/1969 | Scott et al. | 73/819 |
| 3,457,777 | 7/1969 | Nielsen | 73/84 |
| 3,505,860 | 4/1970 | Bishop et al. | 73/819 |
| 3,610,032 | 10/1971 | Di Crispino | 73/819 |
| 3,616,685 | 11/1971 | Strom | 73/819 |
| 3,635,078 | 1/1972 | Wissa | 73/89 |
| 3,728,895 | 4/1973 | Shaw | 73/94 |
| 3,820,385 | 6/1974 | Cordoba | 73/84 |
| 3,881,345 | 5/1975 | Souder | 73/94 |
| 3,975,950 | 8/1976 | Erdei | 73/94 |
| 4,430,890 | 2/1984 | Hains | 73/147 |
| 4,487,056 | 12/1984 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,627,270 | 12/1986 | Jones | 73/38 |
| 4,631,677 | 12/1986 | Park et al. | 364/422 |
| 4,638,447 | 1/1987 | Odeh | 364/556 |
| 4,643,019 | 2/1987 | Jones | 73/38 |
| 4,648,261 | 3/1987 | Thompson et al. | 73/38 |

(List continued on next page.)

FOREIGN PATENT DOCUMENTS

| | | | |
|---|---|---|---|
| 371877 | 6/1990 | European Pat. Off. | 73/38 |
| 252707 | 2/1970 | U.S.S.R. | 73/38 |
| 652266 | 3/1979 | U.S.S.R. | 73/38 |
| 700838 | 11/1979 | U.S.S.R. | 73/38 |
| 794434 | 1/1981 | U.S.S.R. | 73/38 |
| 1409894 | 7/1988 | U.S.S.R. | 73/38 |

OTHER PUBLICATIONS

"Quantitative Determination Of The Mechanical Properties Of Shales," Steiger and Leung, SPE Conference, Oct. 2-5, 1988.
"Predictions Of Wellbore Stability In Shale Formations At Great Depth," Steiger and Leung, SPE Symposium 1989.
"Acoustical Properties Of Clay Bearing Rocks," C. A. Tosaya, 1982.
"Drilling Fluids," Exxon Production Research Company, 1989.
"The Mechanics of Soils," Atkinson et al. 1978, pp. 118-144, 184-209, 292-343.
"Soil Mechanics," Lambe et al., 1969, Chapter 20, pp. 295-303.
"Fundamentals of Potassium Drilling Fluids: A Field Manual to Reduce Drilling and Completion Problems Associated with Hydratable Clays," Steiger, et al., 1985.

Primary Examiner—Hezron E. Williams
Assistant Examiner—Joseph W. Roskos
Attorney, Agent, or Firm—Guy McClung

[57] ABSTRACT

Methods and apparatuses for quantitatively measuring the strengths, pore pressures, and mechanical properties of low permeability geologic materials, such as shales, including test specimen preparation apparatus for adjusting test specimen water content and test apparatus with an end cap having a pore pressure transducer channel disposed adjacent a test specimen filled with an immiscible, inert fluid which does not wet the test specimen, and controlling the deviatoric load on the test specimen during the test to prevent premature failure.

29 Claims, 6 Drawing Sheets

U.S. PATENT DOCUMENTS

| | | | |
|---|---|---|---|
| 4,649,737 | 3/1987 | Jones | 73/38 |
| 4,669,299 | 6/1987 | Closmann | 73/38 |
| 4,679,421 | 7/1987 | Barree | 73/38 |
| 4,679,441 | 7/1987 | Johnson et al. | 73/798 |
| 4,710,948 | 12/1987 | Withjack | 378/208 |
| 4,715,212 | 12/1987 | Johanson | 73/38 |
| 4,753,107 | 6/1988 | Reed et al. | 73/38 |
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,884,438 | 12/1989 | Jones et al. | 73/153 |
| 4,885,941 | 12/1989 | Vardoulakis et al. | 73/794 |
| 4,955,237 | 9/1990 | Suzuki et al. | 73/784 |
| 4,957,001 | 9/1990 | Powell | 73/716 |
| 4,961,343 | 10/1990 | Boone | 73/152 |
| 5,018,396 | 5/1991 | Penny | 73/865.6 |
| 5,025,668 | 6/1991 | Sarda et al. | 73/795 |
| 5,025,669 | 6/1991 | Sarda et al. | 73/798 |

METHODS AND APPARATUSES FOR MEASUREMENT OF THE STRENGTHS, PORE PRESSURES, AND MECHANICAL PROPERTIES OF LOW PERMEABILITY GEOLOGIC MATERIALS

BACKGROUND OF THE INVENTION

1. Field of the Invention

This invention is directed to methods and apparatuses for quantitative determinations of the strengths, pore pressures and mechanical properties of low permeability geologic materials, particularly low permeability rock, and, in one aspect, to the measurement of shale strength, including the strengths of hard, illitic sloughing shales and soft, smectitic gumbo shales under varying compaction and water content conditions.

2. Description of Related Art

Subsurface formations encountered in oil and gas drilling are compacted under in situ stresses due to overburden weight, tectonic effects, confinement and pore pressure. Shales make up over 75% of drilled formations and cause over 90% of the wellbore stability problems. When a hole is drilled in a formation, the wellbore rock is subjected to increased shear stresses due to a reduction in confinement at the wellbore face by removal of the rock from the hole.

Compressive failure of the rock near the wellbore will occur if the rock does not have sufficient strength to support the increased shear stresses imposed upon it. However, if the hole is filled with drilling fluid with sufficient density to increase the wellbore pressure or confining pressure to a proper level, the shear stresses imposed on the wellbore rock will be reduced and the hole will remain stable. If the wellbore pressure is increased too much, lost circulation or hydraulic fracturing of the formation will occur as a result of tensile failure of the wellbore rock.

Previous workers have applied classical elastic and elasto-plastic theories, failure criteria and fracture mechanics to model wellbore behavior under different stress conditions. In 1979 an elastic model was used with field data to obtain stress and pore pressure and empirically derived rock strength values to predict wellbore behavior. In 1983, the present inventor and others modeled the behavior of high angle wells at Statfjord Field in the North Sea by using classical theories and field data to obtain stress, pore pressure and empirically derived shale strength data from several of the early wells. The results of that study were published in a report that was widely disseminated throughout the petroleum and rock mechanics communities. The model results provided wellbore stability charts that showed the proper wellbore pressures or equivalent drilling fluid weights or densities required to prevent wellbore collapse and lost circulation as a function of hole angle and depth. The wellbore stability charts were used as engineering guidelines for subsequent wells and saved many millions of dollars by reducing trouble costs due to wellbore failure. This case and subsequent cases showed that if shale strength data were available, a wellbore model could be used on initial wells in an area to diagnose and predict wellbore behavior and to prevent expensive stuck pipe problems and high trouble costs. Others recognized the importance of this approach and emphasized the need for shale strength data. Physical measurements of shale properties are required to develop realistic failure criteria (shale strengths) and constitutive relationships to effectively understand and define shale behavior under downhole conditions.

The term "shale" includes extremely low permeability clay-bearing rocks. Shales are extremely difficult to test for several reasons. They contain hydratable clays that make them water sensitive and cause them to take up water and swell when exposed to water. Uncontrolled hydration or drying can cause rapid deterioration of the rock structure making it difficult to obtain and maintain sample integrity. Water contents of the shales can be quite variable. In addition, shales have extremely low permeabilities that are in the microDarcy to nanoDarcy range. Permeability is the ease with which fluids can move between voids in a material. Permeability is defined as the capacity of a formation to transmit fluids with the unit of measurement thereof being the "Darcy". One Darcy is defined as that permeability permitting a fluid of one centipoise viscosity to flow at a rate of one cubic centimeter per second through a cross-sectional area of a square centimeter when the pressure gradient is one atmosphere per centimeter. The formula generally used to determine rock permeability is:

$$K = \frac{QU}{A(P/L)}$$

where:
K = permeability in Darcys
Q = quantity of flow
U = viscosity of fluid
A = area of cross-section of core
L = length of core
P = applied fluid pressure.

The results of this equation is in milliDarcys (1/1000 of a Darcy.)

Using standard routine prior art methods and equipment, measured values range from as low as 0.1 milliDarcy to as high as 20,000 milliDarcys. Special prior art pressure-pulse techniques can measure values in the nanoDarcy range (about one billionth of a Darcy). Shales are usually referred to as impermeable rocks and thus have been precluded from direct triaxial testing. Much triaxial strength testing has been done on higher permeability rocks, such as sandstones, clays and soils. Sandstones have permeabilities to water in the Darcy to milliDarcy range; clays and soils in the Darcy to microDarcy range. For example, consolidated sodium montmorillonite clay, one of the least permeable clays, has a permeability of about 10 microDarcys.

The prior art related to the more permeable rocks and soils teaches that the shear strength of the rock generally varies as a function of the mean effective stress (or effective confining stress). Shear strength or the shear stress at failure versus mean effective stress for the porous rock is called its failure criterion or constitutive relationship for failure. The principle of effective stress is recognized as the keystone of modern soil mechanics and was developed by Terzaghi ["Soil Classification for Foundation Purposes," Trans. 1st Int. Cong. Soil Sci., Washington D.C., 1927, Deemer, R.B., Ed., 1928, 4, 127]. The principle states that the stress at any point in a saturated soil mass can be described by the effective stress, $\sigma'$, which represents the intergranular stress between solids of the soil or rock or the difference between the total stress, $\sigma$, and the pore pressure, u, as follows:

$$\sigma' = \sigma - u$$

According to the effective stress concept, all the measurable effects of a change of stress, such as compression and change of shearing resistance are exclusively due to changes in the effective stresses. In the simplest terms, the effective stress principle asserts that the effective stress controls volume change and strength. The significance of the effective stress concept to soil mechanics is that macroscopic deformation behavior is governed by effective rather than total stresses.

The recognition of the effective stress principle had provided a valuable tool to explain soil and rock behavior and has led to the development of many useful failure criteria, unified soil constitutive relationships, such as critical state soil mechanics, [Atkinson, J. H. and Bransby, P. K., *The Mechanics of Soils*, McGraw-Hill (UK), London (1978) 184–234] and stress path analysis [Lambe, T. W., "Stress Path Method," ASCE, JSMFD, 93, SM6 (1967) 309–331]. However, there was (e.g. in 1960) a general belief among some researchers that the effective principle is not valid for shales. That is because shale permeabilities are so extremely low that their pore spaces are ill-defined and possibly not adequately interconnected to provide pore pressure equilibrium or direct measurement. Some believe that pore pressures can not be measured or defined in shales.

It has been a point of controversy as to whether or not low permeability shales (often called impermeable shales) also follow an effective stress relationship. Limited experimental evidence has been previously obtained by indirect methods that indicate that they may. In 1982, Tosaya ["Acoustical Properties of Clay Bearing Rocks," Ph.D. Thesis, Stanford University (1982)] demonstrated indirectly the effective stress principle for shales. In her experiment, acoustic velocities in isostatically loaded shale samples were found to correlate with effective stresses, but not total stresses. The effective stresses were derived from long-term experiments in which pore pressure was externally applied via a line connected directly to the sample and an isostatic total stress applied to the outside of the jacketed sample. Then acoustic velocities were measured on the equilibrated sample. Several such long-term experiments produced excellent correlations with effective stress. However accurate, direct pore-pressure measurements on low permeability shales during triaxial tests have not been made on an equilibrium basis. Standard triaxial test procedures used for higher permeability rocks and soils have not produced good results when applied to low permeability shales.

Conventional tests for measuring properties of rocks, under a triaxial state of stress in which stresses act simultaneously along three orthogonal axes of a specimen, are often conducted in a pressure vessel called a triaxial test cell that contains the specimen and a confining fluid and receives a piston to extend into the vessel. The test cell is typically sufficiently large and open to admit the specimen and confining fluid. A hydraulic pump compresses the confining fluid surrounding the specimen, applying an all-around hydrostatic or isostatic stress to the specimen. An axial loading force is applied to the loading piston that moves into the test cell applying a deviatoric axial (triaxial) stress to the test specimen which is greater than a hydrostatic stress exerted on the sample by the pressurized fluid.

In a conventional triaxial test apparatus for rock testing, the sample is deformed by gradually increasing the axial load until the peak strength of the specimen is reached at which point it fails; i.e., it will not sustain any further increased axial loading. The pore pressure within the sample is measured by a pressure gauge or transducer outside the test cell that is attached to a pore pressure line that runs into the test cell through the end cap to the rock face. Due to the relatively high permeability of the rock, pore pressure equilibrium within the rock and at the pressure gauge or transducer can be achieved rather quickly. Thus the pore pressure response can be fast and monitored easily. Alternatively, pore pressure can be applied and controlled externally during a test by pumping water into the sample through the pore pressure line. The loading stage of the conventional test can be relatively fast and typically at high strain rates in the range of $10^{-2}$ to $10^{-4}$ sec$^{-1}$ and sometimes as slow as $10^{-5}$ to $10^{-6}$ sec$^{-1}$ and still achieve pore-pressure equilibrium during the test. Additionally, highly accurate control of the strain rates is not critical and usually not achieved for the typical high strain rates used for higher permeability rocks. An LVDT (linear variable differential transformer) on the load piston is usually used to control the strain rate, however more recent applications have used LVDT's on the rock or end caps to obtain more precise control.

In our prior art efforts to measure shale strengths, many triaxial tests were performed on several shale types with direct pore-pressure measurements under equilibrium conditions to demonstrate directly that shales follow the general effective stress relationship. This technical achievement preceded work in generalizing the mechanical behavior of shales using effective stress methods. Thus, if the relationship between effective stress and strength, compressibility or expansability is determined experimentally, then the in situ behavior of shales can be predicted. These efforts are described in "Quantitative Determination of the Mechanical Properties of Shales," Paper presented at the 63rd Annual Technical Conference and Exhibition of the Society of Petroleum Engineers, Oct. 2–5, 1988.

As our prior art teaches, it is known to cut water-sensitive shale test specimens from undisturbed block samples under controlled humidity conditions with an inert coring fluid to prevent damage. Sample size is chosen to optimize water content equilibrium and pore pressure equilibrium. The water contents of the shale test specimens are adjusted under equilibrium conditions in a humidity chamber to obtain predetermined water contents without causing damage to the rock. The size of the sample is chosen to minimize the time period required to reach an equilibrium water content, yet large enough to be representative of the rock tested. All subsequent handling of the core prior to testing is done in a controlled humidity chamber to preserve the core. The shale test specimens are in the shape of a small core (right circular cylindrical core). The sample size is chosen also to allow pore pressure equilibrium to be established throughout the sample and with the pore pressure transducer while loading the rock at strain rates that will allow the tests to be conducted in a reasonably short time period, i.e. within about 1–3 days. Thus actual equilibrium pore pressure values can be measured continuously throughout the triaxial test. The pore pressure is measured in the tests by a triaxial end cap that incorporates an accurate miniaturized pressure transducer into the end cap near the rock face. Additionally, it obviates external contact with water from a pore pressure line and thus preserves the original water content of the test specimen throughout the test. It is a stiff assembly that provides accurate pore pressure measurements and maintains volumetric control over the water in the test specimen. The diameters of the end caps are matched to the diameter of the test specimens. The end caps typically have flow channels or grooves therearound and thereacross on the face of the end cap connected to the pore pressure line opening. The small-volume channel between the rock face and the pore pressure transducer is filled with an inert fluid to provide direct pressure transmission and to prevent water drainage from the rock. The sample core is mounted between the end caps and sealed in an impermeable flexible jacket. The sample core mounted between the end caps is instrumented to measure accurate axial and orthogonal transverse strains during the tests by a computerized data acquisition system. Various such systems are available. A conventional heavy duty, high load capacity triaxial test load from with a high pressure confinement vessel (or cell) is used. The system is outfitted with a computer control and data acquisition system. A computer program provides very accurate data acquisition and control of the triaxial test equipment during a test. Precise computer-controlled axial loading of the test specimen is accomplished by a feedback loop that is based on actual strain measurements on the rock. "Strain" is defined as the compression (positive) or extension (negative) resulting from the application of external stresses divided by the original dimension; e.g. axial strain is the fractional change in length of the core specimen The computer control system provides continuous, accurate, strain rates from $10^{-2}$ to less than $10^{-8}$ sec$^{-1}$. This feature provides a capability to simulate extremely stiff load frame characteristics and allows complete stress-strain measurements past peak failure to residual or ultimate stresses to be obtained. It also provides the capability to load the rock at a rate slow enough to obtain equilibrium pore pressure, stress and strain measurements throughout the test.

There has long been an need for methods and apparatuses for measuring the strengths and mechanical properties, including (but not limited to) pore pressure, geologic materials, including but not limited to, low permeability rock, including shales. There has long been a need for a test in which the effective stresses of a low permeability rock can be accurately measured during the test. There has long been a need for a test apparatus and method with which sample equilibrium can be achieved in a practical amount of time. There has long been a need for methods and apparatuses for making quantitative determinations of the strengths and mechanical properties of low permeability rock with which air, which could adversely affect the test results, is not entrapped in the apparatus. There has long been a need for such a test in which fluids are employed which are not miscible with water or with the pore fluid will not wet or react with the test specimen. Also there has long been a need for a test in which the mean effective stress of a low permeability rock can be controlled by adjusting the amount of water in the sample before the test and a test in which mean effective stress can be varied by adjusting the amount of water in the sample prior to testing. There has long been a need for such tests in which a minimal amount of pore fluid is expelled from a sample during testing so that the sample's water content is maintained almost constant while pore pressure is measured directly.

SUMMARY OF THE PRESENT INVENTION

The present invention teaches methods and apparatuses for determining the strengths, mechanical properties, and the pore pressure of low permeability geologic materials, including but not limited to, low permeability rocks, such as shales. In one embodiment, the mechanical test procedure utilizes a triaxial test apparatus with an end cap design that utilizes a miniature pore pressure transducer in communication with a small diameter pore pressure channel filled with a fluid that will not wet or react with the sample and that is immiscible with the pore fluid, i.e. an immiscible nonwetting inert fluid. With this apparatus, the following information can be obtained from a single test: (1) shear strength as a function of mean effective stress; (2) axial, transverse and volumetric strains as functions of load and of mean effective stress; and (3) other functions derived therefrom (e.g. elastic moduli, Poisson's ratio, etc.).

In one embodiment, end caps with flat polished surfaces and diameters closely matched to the sample cores are used. One of the end caps according to the present invention contains an accurate miniature pore pressure transducer in a fluid chamber or port filled with a nonwetting inert fluid immiscible with water or pore fluid which will not wet the sample being tested [e.g. silicone oils, silicone greases, liquid metals (e.g. gallium, mercury)]. The end cap has a stiff, small diameter pore pressure channel connected to the fluid port. The pore pressure channel, in one embodiment, is cylindrical and has a diameter of about 0.03 inches to about 0.08 inches, with a preferred diameter of about 0.04 inches and a fluid volume of about 0.011 cubic centimeters. The fluid port, in one embodiment, is cylindrical and has a diameter of about 0.300 inches and a fluid volume of about 0.11 cubic centimeters. The pore pressure transducer has a diameter of about 0.250 inches. It is preferred that volumes are no larger than about 0.11 cubic centimeters. The stiff end cap can be constructed from titanium, or other high strength materials. In certain embodiments, the volume of the pore pressure channel and fluid port are relatively small, permitting tests on low permeability rocks, such as shales, to be conducted with only a minimal amount of expelled fluid so that the water content of the sample is maintained almost constant during the test.

In another embodiment a triaxial test apparatus is like that previously described except the bottom end does not have a pore pressure transducer and the channels and ports related thereto; rather the bottom end cap has a narrow channel which can receive expelled sample fluid, the narrow channel in communication with a pressure chamber outside the housing via a stiff conduit, the chamber having a pore pressure transducer therein. This is not the most preferred embodiment.

As disclosed in the co-pending application co-owned with the present application entitled "Test Apparatuses And Methods For Adjusting A Material's Fluid Content And Effective Stresses" flow of sample fluid expelled from a sample may be facilitated by providing a wire screen mesh or screens around the sample prior to installing flexible jackets on it. The screens create a flow path whereas the flexible jackets alone impede flow. By using multiple screens secured together, e.g. by spot welding, fine mesh screens to the outside, i.e. facing the sample and the flexible jacket, can inhibit the sample or the jacket moving into the mesh while an inner coarser mesh screen facilitates fluid flow down the sample and into a pore pressure channel.

It should be understood that although preferred embodiments of the present invention are directed to handling, mounting, and testing rocks, including shales, the present invention includes within its scope the handling, mounting, and testing of low permeability geologic materials. Also, although preferred embodiments presented herein discuss triaxial tests, it is to be understood that the present invention includes within its scope other tests, operations, or handling procedures for such geologic material, including but not limited to, tests for measuring and monitoring pore pressure.

It has been discovered that the relationship between water content and mean effective stress for shales, as had previously been found for clays, soils and high permeability rocks such as sandstone, is a functional relationship. For the same rock, the mean effective stress increases with a decrease in water content. Hence, the effective stress of a sample can be varied or controlled by adjusting the amount of water in the sample before the test.

According to the present invention compression tests are conducted that define a water content and a mean effective stress relationship $(w-p')$. The tests start with obtaining a well preserved and undisturbed rock sample cored from a wellbore. Then, a constant isostatic confining pressure, p, is applied on the rock sample in the triaxial cell. Pore pressure, u, is measured by the pore pressure transducer in the fluid port and the mean effective (confining) stress, $p'$, is defined as $(p-u)$.

According to the present invention, our prior art process and apparatus, described previously, are modified. An immiscible, non-wetting inert fluid is employed which will not wet the test sample by either capillary action or by chemical absorption during the test; e.g. silicone oils, silicone greases, and liquid metals (gallium, mercury). The relative humidity of the sample is precisely controlled, adjusted and varied so that a range of data for different relative humidities and different water content levels may be obtained. This is accomplished by employing chemicals, e.g. various salt solutions, to specifically affect the relative humidity in the humidity chamber and in the sample. Vacuum/humidity chambers are used to achieve equilibrium water concentrations without damaging the rock and in a reasonably short period of time. Air entrapped in the sample and in the humidity chamber can cause damage to the sample by microcracking and it also can retard the vapor transport of water into the sample during the adjustment process. The various salt solutions in each humidity chamber provide precise relative humidity values. The space above the solutions and around the rock samples are then evacuated to remove all air. The rock samples then equilibrate with water vapor at the predetermined relative humidity to adjust to a constant water content. The water contents for a particular clay bearing rock sample will increase with increasing relative humidity on a consistent reproducible basis. Thus, a rock sample can be prepared with a predetermined quantitative water content without damage to its structure. The sample is removed from the vacuum/humidity chamber and, preferably, placed in a "glove box" in which it can be manipulated without adversely changing its water content and in which one or more flexible, impermeable jacket (e.g. two similar jackets; a thin jacket and a thick jacket; a rubber jacket and a urethane jacket) and end caps can be applied to the sample. Some air may diffuse into the sample while transferring it to a test apparatus. To insure that there is little or no free air in the rock sample during the test, the water content of the rock is adjusted, as described above, so that it is unsaturated and then, in the first stage of the triaxial test, the rock is isostatically loaded or compressed until it is saturated or until all the free air in the pore space is dissolved into the pore water in the sample. The prior art shows that that can be achieved at relatively low pressures as shown by the equation:

$$u_a = 725 \left( \frac{1 - S_o}{S_o} \right)$$

where $u_a$ is the air pressure or pore pressure in pounds per square inch, required to solubilize all of the air into the pore water and $S_0$ is the initial (fractional) degree of water saturation. To insure that no air is entrapped in the test apparatus, the bottom end cap of the test apparatus is evacuated with a vacuum pump prior to the introduction of the immiscible non-wetting inert fluid. This can be accomplished by emplacing a sealable hollow member over the bottom end cap; sealing it thereon; vacuum pumping the air out of the hollow member, out of the pore pressure channel, and out of the fluid port through a first line; and then, while holding the first line shut, introducing the inert fluid e.g. by gravity and by the action of the vacuum, from second line into the pore pressure channel and fluid port or chamber. Upon removal of the hollow member from the end cap, the pore pressure channel and fluid port are filled with the inert fluid. A flexible impermeable jacket made from e.g., (but not limited to) urethane can be placed around a core sample by placing the jacket within a cylindrical vacuum chamber that holds the jacket open, then placing the core sample within the jacket. Upon removal of the vacuum, the jacket is disposed tightly on the sample. A second jacket can be placed over the first in a similar manner to provide greater strength and to minimize the risk of puncture or failure.

It is, therefore, an object of the present invention to provide new, useful, efficient, unique, and non-obvious methods and apparatuses for measuring strengths and mechanical properties of geologic materials, including, but not limited to, shales.

Another object of the present invention is the provision of apparatus for such measurements which provide accurate data and in which loads are computer controlled so that meaningful data is obtained.

Yet another object of the present invention is the provision of apparatus for the preparation of samples for tests, including, but not limited to, triaxial tests so that pore pressure equilibrium may be reached in a practical amount of time and samples may be prepared undamaged and preserved with certain known and desired characteristics, e.g. water content; absence of air.

A further object of the present invention is the provision of such apparatuses and methods in which immiscible non-wetting inert fluids are used in conjunction with a pore pressure transducer so that the sample being tested will not be adversely affected by the fluid.

An additional object of the present invention is the provision of test apparatuses and methods include expelling a minimal amount of fluid from a test sample during a test to achieve useful results.

A further object of the present invention is the provision of a test apparatus that includes a bottom end cap with a pore pressure channel in communication with a pressure chamber outside of a triaxial test cell housing, the chamber having a pore pressure transducer therein for sensing pressure change in the chamber.

Appended hereto and included herein fully for all purposes are copies of the following patent applications filed on even date with this application, all applications co-owned by the same assignee:

"Methods For Determining In Situ Shale Strengths, Elastic Properties, Pore Pressures, Formation Stresses And Drilling Fluid Parameters" naming Messrs. Ronald P. Steiger and Peter K. Leung as co-inventors.

"Test Apparatuses And Methods For Adjusting A Material's Fluid Content And Effective Stresses," naming Messrs. Ronald P. Steiger and Peter K. Leung as co-inventors.

"Apparatuses and Methods For Measuring Ultrasonic Velocities In Materials," naming Messrs. Ronald P. Steiger and Peter K. Leung as co-inventors.

"Microaccumulator For Measurement Of Fluid Volume Changes Under Pressure," naming Messrs. Ronald P. Steiger, Peter K. Leung, and Rudolf J. Stankovich as co-inventors.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions or further improvements.

DESCRIPTION OF THE DRAWINGS AND PHOTOGRAPHS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings and photographs, which form a part of this specification. It is to be noted, however, that the appended drawings and photographs illustrate preferred embodiments of the invention and are therefore not to be considered limiting of its scope, for the invention may admit to other equally effective equivalent embodiments.

DESCRIPTION OF EMBODIMENTS PREFERRED AT THE TIME OF FILING FOR THIS PATENT

Figure 1:
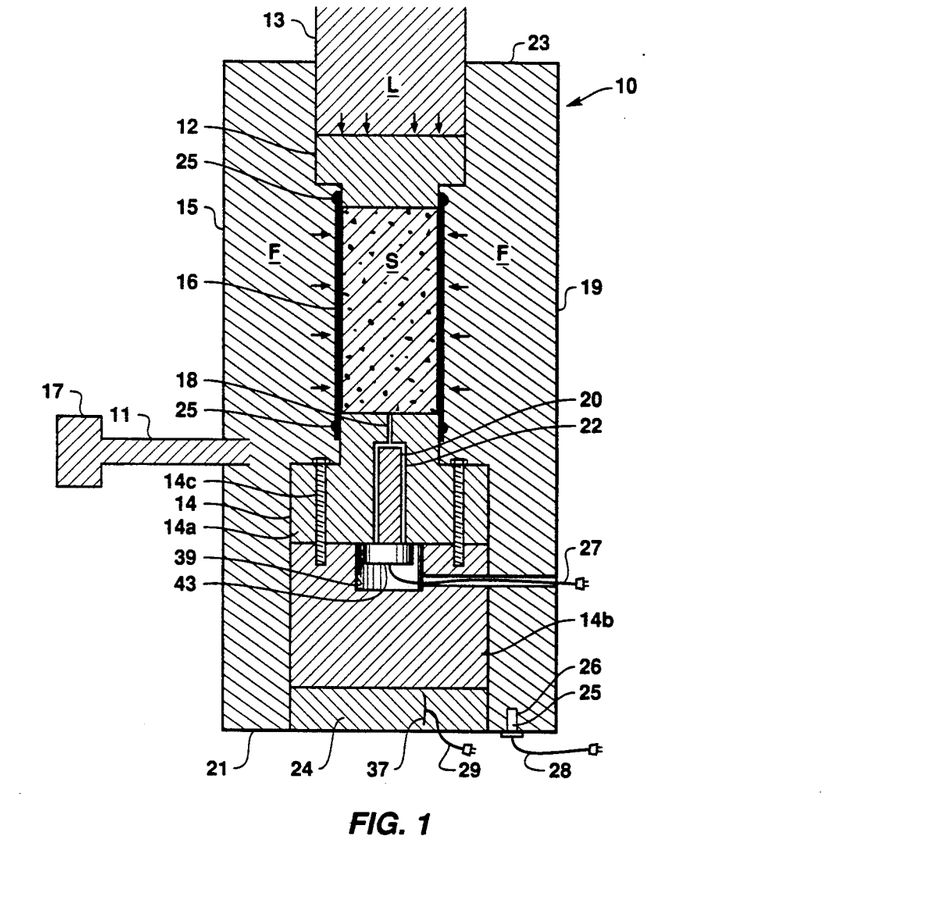
FIG. 1 is a schematic cross-sectional view of a triaxial test apparatus according to the present invention.

As shown schematically in FIG. 1, a triaxial test apparatus 10 according to the present invention has a housing 15 preferably made from titanium or high strength steel with a side wall 19, (preferably generally cylindrical) a bottom plate 21, and a top plate 23. The apparatus 10 has a top end cap 12 and a bottom end cap 14 with a top portion 14a and a bottom portion 14b bolted together by bolts 14c. The bottom portion 14b rests on a load cell 24 that rests on the bottom plate 21. A sample S, placed between the end caps, is sheathed with an impermeable jacket 16. A load piston 13 contacts the top end cap 12 and a portion of the piston extends sealingly through the top plate 23 of the housing 15. The load piston applies a load L to the sample S through the top end cap 12. A confining fluid pumping system 17 pump and hydraulic fluid F into the housing 15 through a fluid line 11. As noted, additional jackets may be used. The end caps are made from high strength materials (e.g. titanium or hardened steel) and the boundaries between the end caps and the jacketed sample are impermeable. The jacket extends slightly beyond the sample on the end caps and wire ropes 25 secure the ends of the jacket about the end caps.

The end caps have flat, polished smooth surfaces for contacting the sample with diameters closely matched to that of the sample; i.e. it is preferred that they be within 0.005 inches of each other. Also, it is preferred that samples' ends' flatness be within about 0.001 inch per inch of diameter. This minimizes void space between end cap and sample; provides uniform loading of the sample; and minimizes unwanted end effects.

The bottom end cap 14 has a pore pressure channel 18 which communicates with a fluid port or chamber 20. A pore pressure transducer 22 is disposed in the fluid chamber 20. The bottom portion 14b has a recess 39 therein to provide an area into which a base 43 of the transducer 22 can extend. A non-wetting inert fluid immiscible in water or pore fluid (e.g. mercury) is placed in the pore pressure channel 18 and in the fluid chamber 20. Preferably, the pore pressure channel 18 and the fluid chamber 20 are vacuum evacuated prior to the introduction of mercury so that no air is trapped therein which could adversely affect test results. The pore pressure transducer 22 is an accurate miniature strain-gauge type pressure transducer interfaced via wiring 27 with a digital data acquisition system monitor/control (e.g. computer).

The hydraulic fluid F surrounding the sample S 12 provides a desired confining pressure for the sample S. A confining pressure transducer 25 mounted in a hole 26 in the plate 21 has wiring 28 leading to the computer.

The load cell 24 has wiring 29 extending therefrom for interfacing with the computer. The load cell 24 has a strain gauge (or gauges) 37 thereon that indicates the amount of axial load applied through the top end cap and to the sample by the piston 13.

Figure 2:
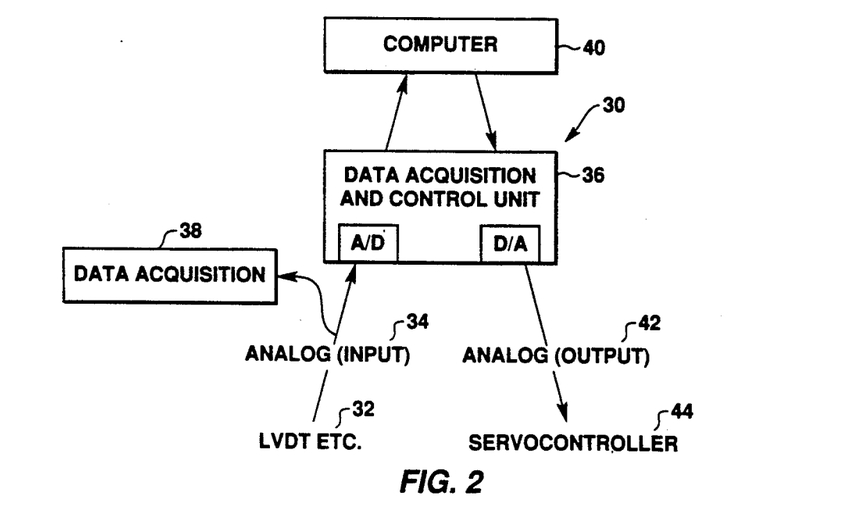
FIG. 2 presents in schematic form a data acquisition system according to the present invention.

Referring now to FIG. 2, a data acquisition and control system 30 is shown which is utilized with an apparatus such as the triaxial test apparatus 10 of FIG. 1 to control the rate of axial loading of a test specimen. An LVDT 32 (or LVDT's; e.g. as the LVDT's in FIG. 8) (or other measuring device such as a pore pressure transducer; confining pressure transducer; or radial strain transducer) provides analog signal input 34 to a data acquisition and control unit 36; e.g. a signal representative of axial strain within a certain time period. Input is also provided to data acquisition 38 for recording axial strain versus axial load. The data from unit 36, in digital form is provided to a computer 40 which compares the axial strain rate or strain within a certain time period to a chosen strain rate and sends a signal in digital form to the unit 36 which, in turn, provides an analog output signal 42 to operate servocontroller (or controllers) 44 which control valves to affect axial load.

Figure 3:
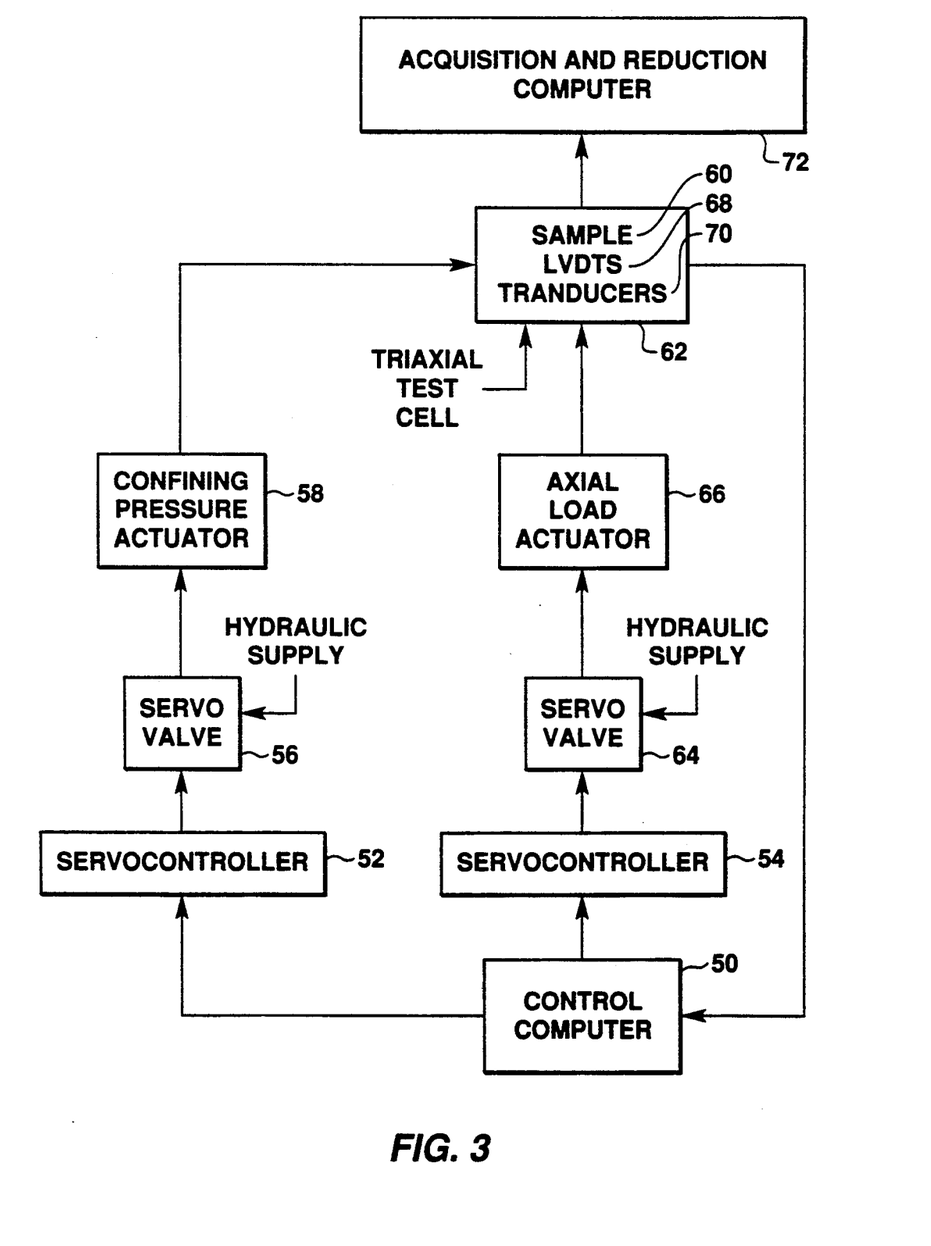
FIG. 3 presents schematically a computer control system according to the present invention.

As illustrated in FIG. 3, a control computer 50 (like the computer 40 of FIG. 2; e.g. an IBM AT PC computer) provides an analog output signal to servocontrollers 52 and 54. The servocontroller 52 controls a servovalve 56 which affects the supply of hydraulic fluid to a confining pressure actuator 58. The actuator 58 provides the pressurized hydraulic fluid about a test sample 60 in a triaxial test cell 62 like the apparatus 10 of FIG. 1.

The servocontroller 54 controls a servovalve 64 which affects the supply of hydraulic fluid to an axial load actuator 66. The actuator 66 provides pressurized fluid to a piston (not shown) which imparts an axial load to an end cap, such as the end cap 12 of the apparatus 10. The sample 60 may have various LVDT's 68 associated therewith, as well as transducers 70, which sense changes in the sample 60 and provide data to an acquisition and reduction computer 72 (like computer 40 in FIG. 2).

Figure 8:
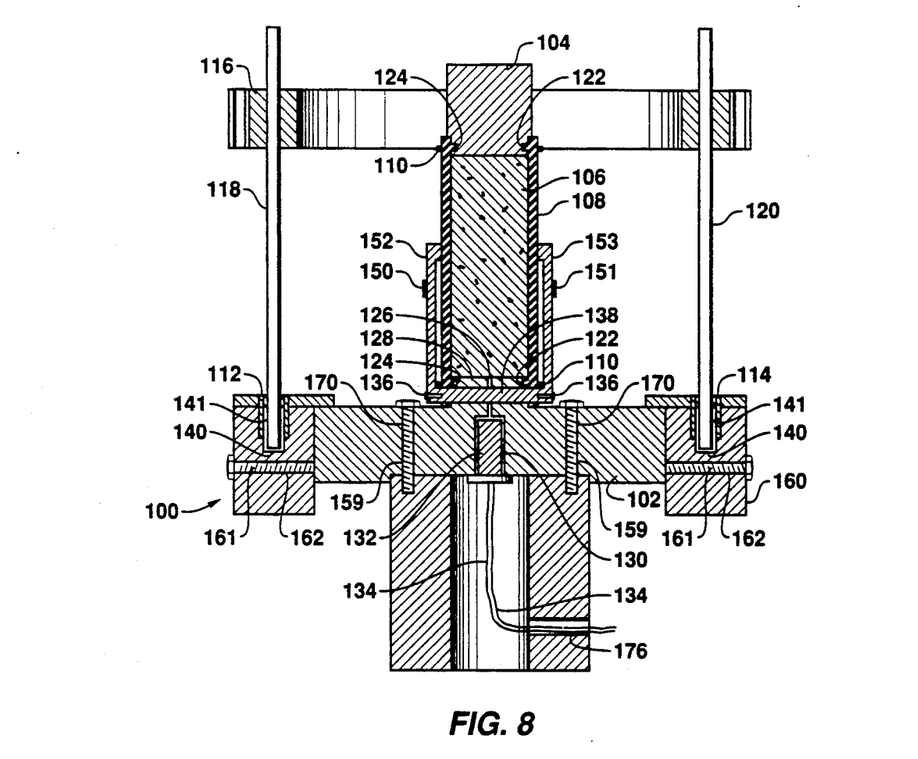
FIG. 8 is a cross-sectional view of a test cell according to the present invention.

As shown in FIG. 8, a triaxial test cell apparatus 100 according to the present invention has a bottom end cap 102 and a top end cap 104. A core sample 106 is mounted on the bottom end cap 102 and beneath the top end cap 104. A flexible impermeable jacket 108 sheaths the sample 106 and extends slightly beyond it onto each end cap, and wire ropes 110 secure the jacket to the end caps so that an impermeable boundary is formed between the end caps and the sample. Lips 122 of the jacket 108 (or jackets if used) are received within corresponding grooves 124 in the end caps.

LVDT's 112 and 114 are disposed between the end caps and movably extend through holes 140 in a bottom collar 160 secured to the bottom end cap by set screws 161 through holes 162. LVDT rods 118 and 120 are secured to an LVDT holder 116 that is secured to the top end cap 104. The LVDT's (112, 114) indicate vertical movement of the end cap 104 due to axial movement (deformation) of the sample 106. The rods 118, 120 of the LVDT's are moveable in coils 141 in the bottom collar 160.

A pore pressure channel 126 extends from a top 128 of the bottom end cap 102 into a pore pressure chamber or port 130 in which is disposed a pore pressure transducer 132. Wiring 134 extends from the pore pressure transducer into the base 172 and out through a sealed lead-in aperture 176 for interfacing the transducer with other equipment, e.g. a computer or other control/monitor/recording system. Screws 136 secure a radial strain gauge ring 138 about the bottom end cap 102. Radial strain gauges indicate radial deformation of the test sample specimen. Cantilevered strain gauges 150, 151 are secured to arms 152, 153 which in turn are secured to the radial strain gauge ring 138. Wiring 146 is interconnected with and extends from the gauges 150, 151 (and others not shown) to the monitor/control computer. Holes 159 in the bottom of the end cap are for bolts 170 to mount the end cap to a bottom 172 base.

The apparatus 100 can be enclosed within a housing, not shown (such as the housing 15, FIG. 1) and used with a piston, not shown (such as the piston 13, FIG. 1) and a pumping system, not shown (such as the system 17, FIG. 1).

The pressure transducer 132 is a typical commercially available transducer (e.g. Kulite Semiconductor Products, Inc. Model HEM 375-20000A), with a deflectable top portion with a strain gauge mounted thereon and wiring therefrom.

Figure 9:
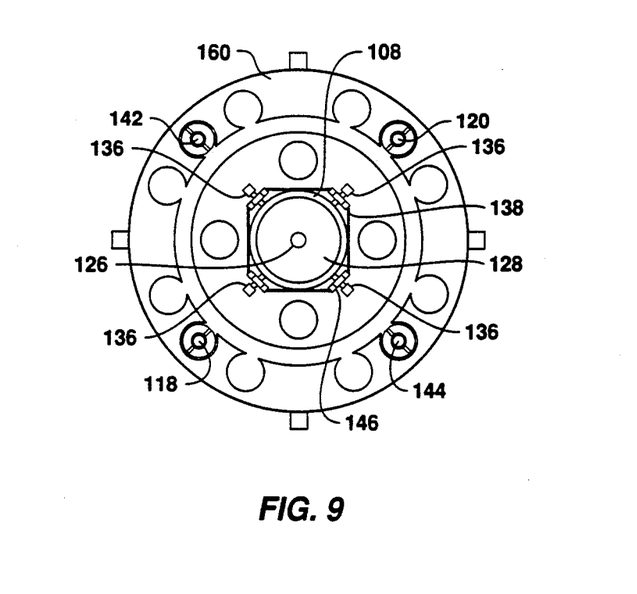
FIG. 9 is a view along line 9—9 of FIG. 8.

Referring now to FIG. 9, the LVDT holder 116 has the rods 118, 120 (shown in FIG. 8) secured thereto and also rods 142, 144 (not shown in FIG. 8) extend. The radial strain gauge ring 138 is secured by the screws 136 to the bottom end cap 102 and the flexible impermeable jacket 108.

Figure 10:
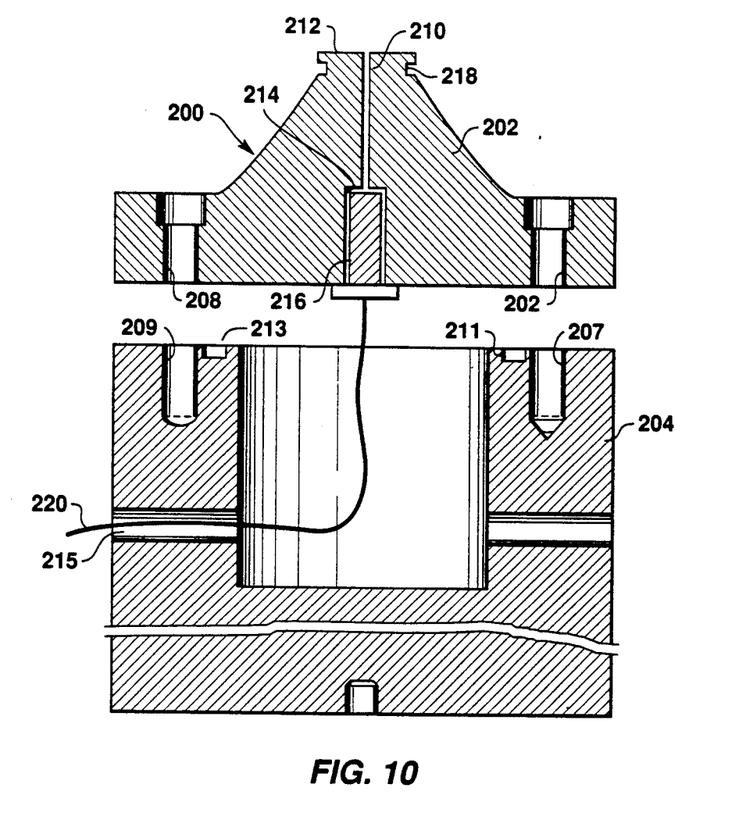
FIG. 10 is a cross-sectional view of an end cap according to the present invention.

FIG. 10 illustrates an end cap 200 for triaxial tests according to the present invention. The end cap 200 has a top plate 202 and a bottom body 204 joinable by threaded bolts (now shown) extending through threaded holes 206, 207 and 208, 209. The seal between the two portions of the end cap is enhanced with an O-ring 213 in a recess 211 in the bottom body 204. A pore pressure channel 210 extends from an apex 212 of the top plate 202 to a pore pressure port 214 in which is disposed a pore pressure transducer 216. It is preferred, for testing shales, that the transducer (like transducer 216) occupy most of the port volume because sample strength is a function of water content and, if water content changes significantly during testing, strength would also vary significantly—resulting in inconclusive data. A groove 218 around the apex 212 can receive and hold a portion of a flexible jacket disposed on a core sample. The transducer 216 includes wiring 220 which extends out from a sealed lead-through 215 in the bottom body 204.

Figure 11:
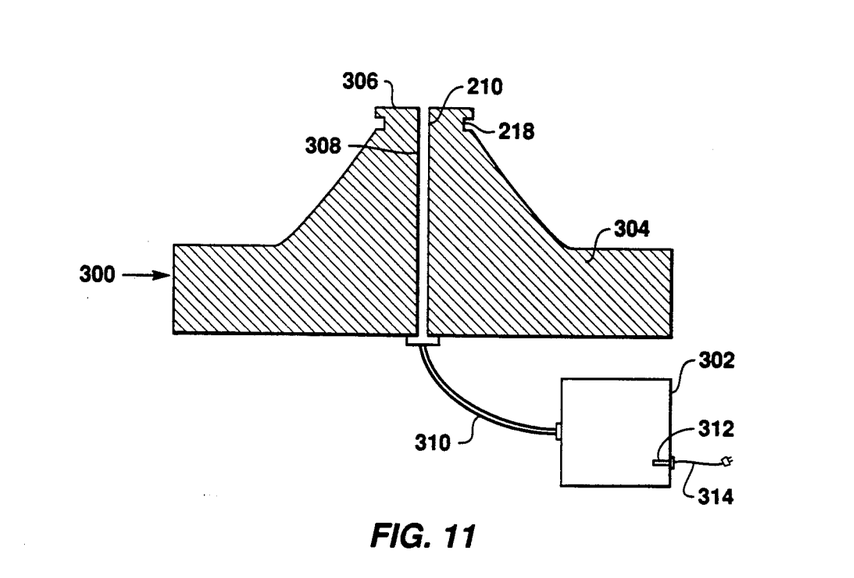
FIG. 11 is a cross-sectional view of an end cap and pressure chamber for a triaxial test apparatus according to the present invention.

FIG. 11 illustrates and end cap 300 and pressure chamber 302 according to the present invention which can be used in place of other end caps (e.g. end cap 14, FIG. 1) in triaxial test apparatus according to the present invention as previously described herein. The end cap 300 has a body 304 with an apex 306 (like apex 212, FIG. 10) and a pore pressure channel 308 therethrough. Although channel 308 is shown as extending from top to bottom of the end cap 300, it is within the scope of this invention for such a channel to exit from a side of the end cap. Fluid expelled from a sample mounted above the end cap 300 can move into the pore pressure channel 308. Via a stiff conduit 310 the pressure chamber 302 is in fluid communication with the pore pressure channel 308. It is preferred that the pore pressure channel 308 and the chamber 302 be filled with an inert fluid not miscible with the fluid in the sample to be tested and a fluid that neither reacts with the sample nor with the sample fluid and which does not wet the sample. For example, if the sample fluid is water, it is preferred that mercury be the fluid in the pore pressure channel and pressure chamber. A pore pressure transducer 312 is mounted in the pressure chamber and wiring 314 extends therefrom for conveying the transducer signals to a monitor system. It is preferred that the pressure chamber have a volume of about 10 cubic centimeters or less, with a volume of about 0.25 cubic centimeters most preferred. A valve 316 controls flow through the conduit 310.

Figure 4:
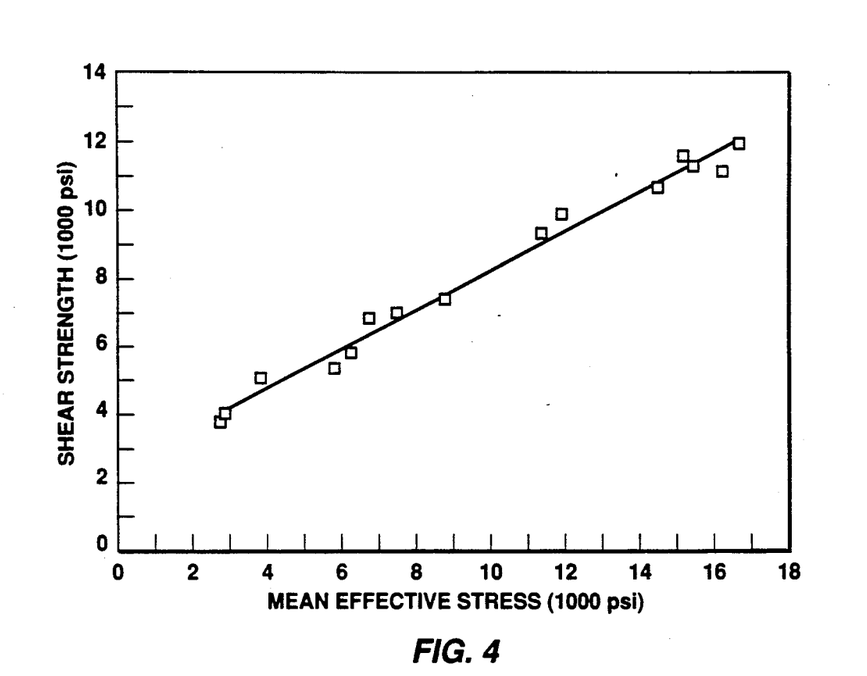
FIGS. 4 and 5 are graphs of data typically obtained by employing apparatuses and methods according to the present invention.

The data presented in FIG. 4 are from tests of a low permeability shale sample. The material is a homogeneous massive clay shale, very uniformly textured, consisting of silt-sized clasts of quartz (10–30%) dispersed in a matrix of foliated clay minerals and carbonate. The actual material to be tested was retrieved from an outcrop area as a 16 inch diameter core preserved at in-situ moisture content. After the shale was obtained, characterization tests were undertaken to further define the properties of the shale to be tested. Characterization samples were cut to about 0.75 inches in diameter by about 1.50 inches in length and then preserved in Saran (TM) wrap and placed inside a 23 cc Teflon (TM) bottle. The water content of these specimens was adjusted later.

In order to determine the mineralogy of the material being tested, thin sections were made and a petrographic analysis and description were done along with clay mineralogy by X-ray diffraction. In thin section, the tested material was found to be composed of 59% clay matrix, 18% detrital quartz, 10% detrital minerals, and 13% secondary carbonate. The X-ray diffraction showed the material to be 36% quartz, 38% clay, 5% dolomite, 12% calcite, 2% feldspar, 4% plagioclase, and 2% pyrite. The clay fraction was 39% illite and 38% mixed-layer illite-smectite (IMII-ordered), with the remainder kaolin, chlorite and smectite.

In situ saturation was 100% with water content levels between 3.8% and 4.2% dry weight. The water contents of the test samples were adjusted to values within the range of 2.85% to 3.8% dry weight prior to the tests. The permeability of the sample material was determined in a permeameter using a transient pulse technique. The sample was tested at hydrostatic confining pressures of 10,000 p.s.i. and 20,000 p.s.i. with permeabilities of 13.5 and 16.8 nanoDarcys, respectively.

Scoping tests were used to determine the strain rates and equilibration time. The strain rate used for testing was $2.0 \times 10^{-7}$ in/in/sec and the equilibration time was up to 20 hours for confining pressures up to 20,000 p.s.i.

Multiple triaxial tests of the sample shale material were conducted at different confining pressures, pore pressure equilibration times, bedding orientations, and strain rates. The confining pressures varied from 3000 p.s.i. to 20,000 p.s.i. The standard strain rate was $2.0 \times 10^{-7}$ in/in/sec, but strain rates from $2.0 \times 10^{-6}$ to $5.0 \times 10^{-8}$ were also used. Mechanical tests were conducted using a triaxial, servo-controlled testing apparatus according to the present invention to subject samples to desired stress states at controlled strain rates. Axial strain was measured using LVDT's and transverse strain by strain-gaged cantilever beam transducers. The stress difference was measured by a strain-gaged load cell on the inside of the vessel. Confining pressure was measured using a pressure transducer, and pore pressure was measured by a transducer on the inside of an endcap according to the present invention.

Strain rates were controlled with a computer equipped with a Data Acquisition and Control Unit (FIG. 2). The data acquisition was done using another computer.

FIG. 4 presents data for shale samples tested with an apparatus as shown in FIGS. 1–3 showing the failure criterion of shear strength (vertical axis) versus mean effective stress (horizontal axis). The nearly linear function displayed by the curve (in this case a straight line) or envelope in FIG. 4 proves that characteristics of shales, e.g. strength and pore pressure, can be measured with a triaxial test apparatus according to the present invention and that shales do conform to a mean effective stress relationship.

The tests for the data presented in FIG. 4 were conducted on shale sample test specimens cut to a special size from undisturbed block samples under controlled humidity conditions with an inert coring fluid to prevent damage. The small core samples were immediately sealed in air-tight containers. The sample diameter ranged from 0.5 to 1 inch or larger with a length to diameter ratio of 2 or larger. An optimum diameter of about 0.75 in. and a length of about 1.50 in. was used for these tests. The test specimens were adjusted under equilibrium conditions in a vacuum/humidity chamber to obtain predetermined water contents without causing damage to the rock. This was done by placing a saturated water and salt solution of known salt concentration in the bottom of the vacuum/humidity chamber with a salt concentration that provides a known relative humidity at a known (e.g. room) temperature; for example, but not limited to, a saturated sodium chloride solution to produce a 75% relative humidity producing a certain sample water content or saturated potassium chloride to produce an 85% relative humidity producing a different sample water content. An alternative to the use of saturated solutions is to use a commercially available controlled humidity chamber that changes only water vapor content (without the use of solids, liquids, or salts). Also, rather than using saturated salt-water solutions, it is within the scope of this invention to use any liquid miscible with water or any materials soluble in water that can produce different relative humidities.

The core sample test specimens were placed in the vacuum/humidity chamber above the salt solution. Then the chamber was evacuated to remove the air. The samples were then allowed to equilibrate with the water vapor in the chamber at the known relative humidity. This takes 1 to 4 weeks or longer depending on the type and nature of the rock. In this case, it took 2 to 3 weeks. The equilibrated samples with a constant water content were then sealed in Teflon TM poly tetra fluoro ethylene "PTFE" material bottles until testing commenced.

Water content of a sample is determined after a test by weighing all or part of the sample and then drying it in an oven. After drying, the sample is again weighed. The resultant weight loss indicates water content. In order to facilitate equilibration within the vacuum/humidity chamber, when initially beginning tests on a particular type of rock, a sample is placed in the chamber for a known time period (e.g., a week or so) and then removed and weighed. The sample is then placed back in the chamber and the process is repeated. Eventually a point is noted beyond which the sample's water content does not increase. That point correlates with a particular time period in the chamber. The sample's equilibrium water content is thereby determined. Therefore, for future samples of this rock, the required time period is known for reaching the known water content for that particular relative humidity.

A pore pressure transducer was mounted in an end cap like bottom end cap 14, FIG. 1. The pore pressure transducer channel was vacuum back-filled with mercury. A sample core was then covered, other than its ends, with an impermeable, flexible rubber jacket and an impermeable flexible plastic jacket and mounted with end caps in a controlled vacuum/humidity chamber. The jackets extended slightly beyond each end of the sample onto the end caps and lips of the jackets were received in a groove of the end caps. A wire rope was secured tightly over the jacket and each end cap to create an impermeable boundary. Strain gauges and LVDT's were then mounted on the end caps and the test sample to provide precise axial and orthogonal strain measurements during the test. The mounted and instrumented sample was placed in the confinement vessel of the triaxial test apparatus and was then isostatically loaded in the confinement vessel at a predetermined pressure of between about 500 to about 15000 p.s.i. and allowed to pressure equilibrate. The pore pressure and strains were monitored continuously with a system as shown in FIGS. 2, 3.

After a pressure equilibrium period within the device while it was being isostatically loaded by confining pressure, usually of about 6 to about 20 hours, a load piston (like piston 13 applying load L in FIG. 1) was brought down to touch the top end cap. This pressure equilibration period allows free air in pores in the sample to go into solution in water in the sample. Thus allowing the pore space to be completely filled with water, i.e., saturated. Otherwise such air would adversely affect test results because the sample would be unsaturated and the pore pressure transducer readings would fluctuate during the axial loading due to measuring air and water pressure in the pore space as air is dissolved into the water during the test. It is preferred that the sample be saturated prior to axial loading so that pore water (or fluid) pressure and thus effective stress can be continuously monitored during the test. Computer controlled axial loading by the piston was commenced at a strain rate of $10^{-5}$ to $10^{-8}$ inch/inch/second that allowed the pore pressure to equilibrate within the sample and at the pore pressure transducer. "Strain" is defined as the compression (positive) or extension (negative) resulting from the application of external stresses divided by the original dimension; e.g. axial strain is the fractional change in length of the core specimen. The required strain rate was determined by initial scoping tests.

Figure 5:
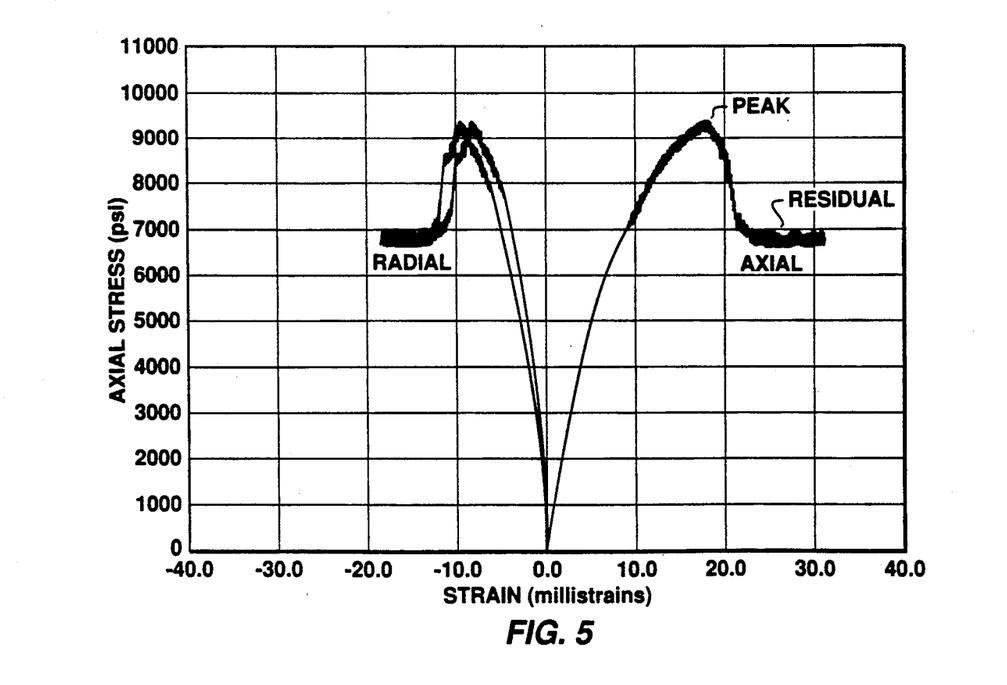

Pore pressure, axial stress (deviatoric load impressed by a load piston), confining stress, axial strain and transverse strains were measured and recorded continuously throughout the test. The sample was loaded past peak stress to a residual stress level or ultimate stress value, or beyond, to obtain a complete stress-strain curve as shown in FIG. 5. After the test, the water content of the test sample was determined and recorded. More tests at different water contents were run on additional samples to obtain the failure criterion of shear strength versus mean effective stress shown in FIG. 4.

Figure 6:
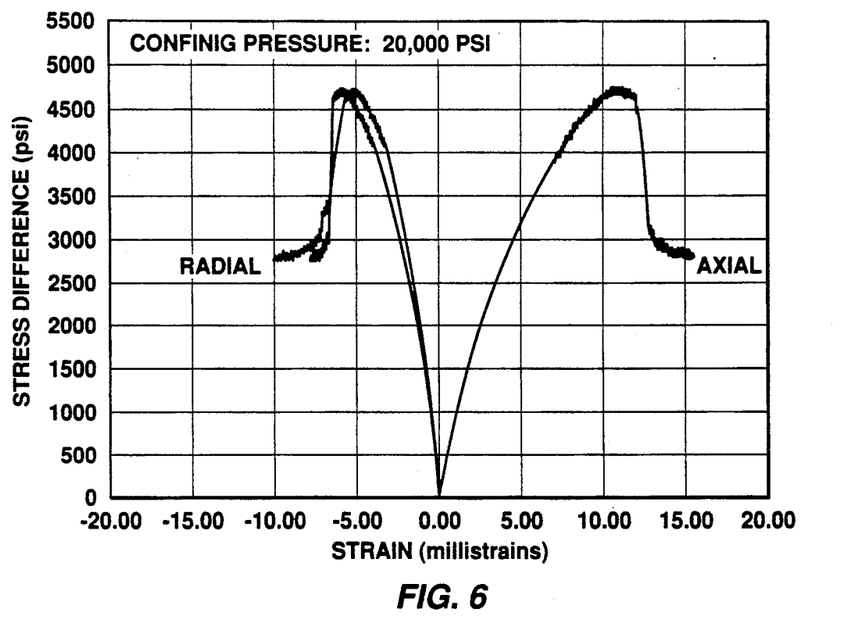
FIG. 6 is a graph of data obtained from a test conducted with apparatuses and methods according to the present invention.

FIG. 6 presents data obtained from a test of a sample of another low permeability shale with apparatus and methods according to the present invention. The test lasted about four days. The confining pressure was maintained at about 20,000 p.s.i. and was held there for 41.4 hours. The pore pressure of the test sample at this confining pressure was 17,777 p.s.i. and the sample water content was 7.61% dry weight (weight of water in the sample divided by weight of the dry sample). The maximum deviatoric stress applied was 4725 p.s.i. and, at this level, the axial strain was 0.0217 or 21.7 millistrains, the transverse radial strain was −0.0109 or −10.9 millistrains, and the pore pressure was 18,630 p.s.i. [A millistrain is one thousandth of a strain or 1/1000 of the dimension being measured.] The horizontal axis in FIG. 6 illustrates both radial strain, to the left of zero, and axial strain, to the right of zero, as a function of the axial stress induced by the load piston.

Figure 7:
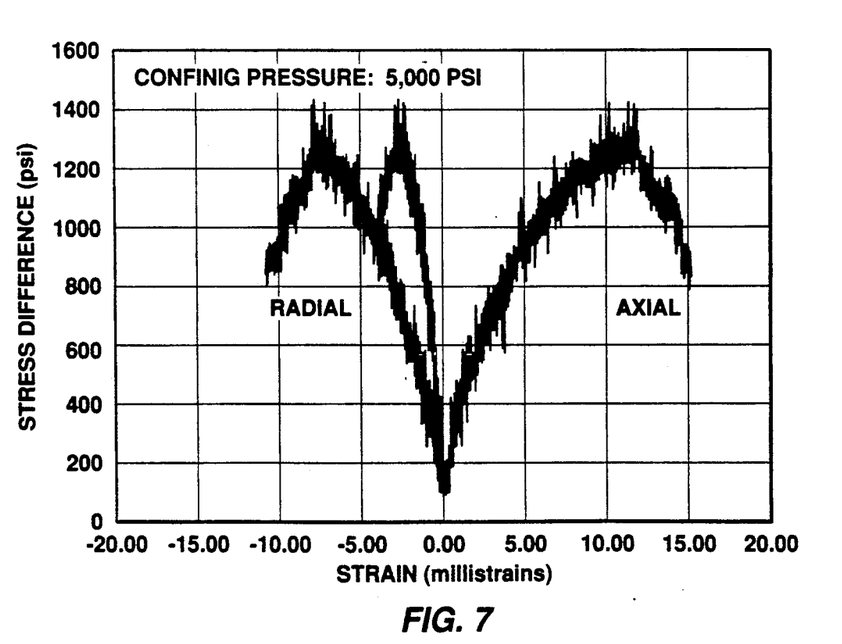
FIG. 7 is a graph, similar to that of FIG. 6, but with results not as well-defined as those presented in FIG. 6.

FIG. 7 presents data similar to that shown in FIG. 6, but with comparatively poorly defined results due to electronic noise in a faulty signal amplifier.

In general, then, it can be seen that according to the present invention a curve or envelope (e.g. a curved line or a straight line; a line representing a functional relationship (e.g. as in FIG. 4) can be determined for various properties of a low permeability geologic material (including, but not limited to, a shale) as compared to the material's mean effective stress.

For example, the present invention includes a method for determining a failure envelope for a low permeability geologic material which includes continuously measuring and recording the material's pore pressure during a process of applying a load to the material; applying a confining pressure during the process of applying the load; measuring and recording the material's strength at different pore pressures; determining the mean effective stress of the material at each different pore pressure; plotting on a two-axis graph a point for each measured strength versus its corresponding mean effective stress; and then determining a curve (the failure envelope) that fits the plotted points. In one embodiment of such a method the material can be a low permeability rock.

Another embodiment is a method for determining an elastic property envelope of a low permeability geologic material which includes continuously measuring and recording the material's pore pressure while applying a load to the material; applying a confining pressure to the material while applying the load to it; measuring and recording axial and radial strains of the material while applying the load; determining the material's mean effective stress for each different pore pressure; determining a value (e.g. by using known equations and methods) of the material's elastic property (e.g. bulk modulus, shear modulus, Young's modulus, Poisson's ratio, etc.) for each different mean effective stress; plotting on a two-axis graph a point for each elastic property value versus its corresponding mean effective stress; and then determining a curve (elastic property envelope) that fits the plotted points. In one embodiment of this method the geologic material can be a low permeability rock.

The present invention also teaches a method for determining an elastic-plastic stress-strain envelope (three-dimensional) for a low permeability geologic material which includes continuously measuring and recording the material's pore pressure while applying a load to the material; applying a confining pressure to the material while applying the load to it; monitoring and recording load stress from the load on the material; monitoring and recording radial and axial strains on the material while applying the load; determining the mean effective stress of the material for each different pore pressure; plotting in a three-axis system a point for each load stress versus each of its corresponding strains and mean effective stress; and then determining an envelope (load stress-strain-mean effective stress envelope) that fits the points thus plotted. In one embodiment of this method the geologic material can be low permeability rock.

As disclosed in the copending application entitled "Test Apparatus And Methods For Adjusting A Material's Fluid Content and Effective Stresses," it is possible to utilize a top end cap with the methods and apparatuses of the present invention which also has a pore pressure channel, a pore pressure transducer, and their related attachments and devices.

Within the scope of this invention are methods and apparatuses for measuring pore pressure with a body having a pore pressure channel and a pore pressure transducer therein, the body disposable against a face of a geologic sample so that sample fluid expelled from the sample when a load is applied to it flows into the pore pressure channel contacting an inert fluid filling the pore pressure channel and compressing it, this compression sensed by a pore pressure transducer in the channel which transmits a signal to a monitor-recording system. Such apparatuses can be used in situ, e.g. in wellbores, tunnels, mines, etc.

Preferred embodiments have been described for "triaxial" tests. As used in the appended claims it is intended that this term include multi-axial (i.e. in more than one axis) tests.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. Triaxial test apparatus for testing rock samples in a housing fillable with confining fluid for providing confining pressure on a sample to be tested, the sample having a top and a bottom, the housing having a channel for introduction therein and removal therefrom of the confining fluid, the housing having an opening therethrough through which a portion of a load piston sealingly extends for providing a load on the sample, the traixial test apparatus comprising
sample mounting means for mounting the sample within the housing, the sample mounting means including a top end cap for mounting at the top and a bottom end cap for disposition at the bottom of the sample,
the bottom end cap housing a body and a pore pressure channel in the body in fluid communication with the bottom of the sample and into which flows sample fluid expelled from the sample during testing, the sample fluid contacting an inert fluid in the pore pressure channel,
a bottom end cap chamber in the body of the bottom end cap in fluid communication with the pore pressure channel, the bottom end cap chamber for containing an amount of the inert fluid,
a pore pressure transducer disposed in the bottom end cap chamber for reacting to and sensing changes in the amount of sample fluid expelled from the sample during testing,
wiring connected to the pore pressure transducer and extending therefrom and out of the body, the wiring connectible to a system for monitoring and recording changes sensed by the pore pressure transducer,
the pore pressure channel and the bottom end cap chamber filled with the inert fluid, the inert fluid immiscible with the sample fluid,
at least one flexible impermeable jacket for enclosing the surface of the sample other than its ends and preventing the confining fluid from directly contacting the sample and preventing sample fluid from being expelled from the portion of the sample covered by the jacket, and
the bottom end cap suitable for mounting on a load cell mounted within the housing.

2. The triaxial test apparatus of claim 1 wherein the sample fluid is water and the inert fluid is mercury.

3. The triaxial test apparatus of claim 1 wherein substantially all air is evacuated from the pore pressure channel and the bottom end cap chamber.

4. The triaxial test apparatus of claim 1 wherein the top end cap and the bottom end cap each has
a substantially flat planar surface for contacting the sample.

5. The triaxial test cell apparatus of claim 4 wherein the flatness of the end caps varies no more than about 0.001 inches per inch of width.

6. The triaxial test cell apparatus of claim 1 wherein the jacket extends partially over each end cap and is secured thereto.

7. The triaxial test cell apparatus of claim 1 including also indicating means in contact with the sample for indicating a change in a dimension of the sample, the indicating means having wiring connected thereto and connectible to a monitor/control system.

8. The triaxial test cell apparatus of claim 7 wherein the indicating means includes
one or more linear variable differential transformers.

9. The triaxial test apparatus of claim 1 wherein the volume of fluid in the bottom end cap chamber when the transducer is present therein is no larger than about 0.11 cubic centimers and the pore pressure channel's volume is no larger than about 0.11 cubic centimeters.

10. The triaxial test apparatus of claim 1 wherein the sample to be tested is low permeability rock.

11. Triaxial test apparatus for testing low permeability rock samples in a housing fillable with confining fluid for providing confining pressure on a sample to be tested, the sample having a top and a bottom, the housing having a channel for introduction therein and removal therefrom of the confining fluid, the housing having an opening therethrough through which a portion of a load piston sealingly extends for providing a load on the sample, the traxial test apparatus comprising
sample mounting means for mounting the sample within the housing, the sample mounting means including a top end cap for mounting at the top of the sample and a bottom end cap for disposition at the bottom of the sample,
the bottom end cap having a body and a pore pressure channel in the body in fluid communication with the bottom of the sample and into which flows sample fluid expelled from the sample during testing, the sample fluid comprising water and contacting an inert fluid comprising mercury in the pore pressure channel, a pore pressure chamber in the body in fluid communication with the pore pressure channel and into which flows sample fluid from the pore pressure channel, substantially all air removing from the pore pressure channel and pore pressure chamber, a pore pressure transducer disposed in the pore pressure chamber for reacting to and sensing changes in the amount of sample fluid expelled from the sample during testing, the pore pressure chamber's volume of fluid therein when the transducer is present therein is no larger than about 0.11 cubic centimers, wiring connected to the pore pressure transducer and extending therefrom and out of the body, the wiring connectible to a system for monitoring and recording changes sensed by the pore pressure transducer, the pore pressure channel and the pore pressure chamber filled with the inert fluid, at least one flexible impermeable jacket for enclosing the surface of the sample other than its ends and preventing the confining fluid from directly contacting the sample and preventing sample fluid from being expelled from the portion of the sample covered by the jacket, the jacket extending partially over each end cap and secured thereto, the bottom end cap suitable for mounting on a load cell mounted within the housing, the top end cap and the bottom end cap each having a substantially flat planar surface for contacting the sample, and indicating means in contact with the sample for indicating a change in a dimension of the sample, the indicating means including one or more linear variable differential transformers to indicate a dimensional change in the sample, the transformers having wiring connected thereto, the wiring connectible to a monitor/control system.

12. An end cap for disposition at an end of a rock sample to be tested in a triaxial test apparatus, the end cap comprising, a body having a top and a bottom, a pore pressure channel in the body in fluid communication with the top of the body and into which sample fluid expelled from the sample during testing can flow, a pore pressure chamber in the body in fluid communication with the pore pressure channel, the pore pressure chamber fillable with an inert fluid immiscible with the sample fluid, a pore pressure transducer disposed in the pore pressure chamber for reacting to and sensing changes in the amount of sample fluid expelled from the sample during testing, and wiring connected to the pore pressure transducer and extending therefrom and out of the body, the wiring connectible to a system for monitoring and recording changes sensed by the pore pressure transducer.

13. The end cap of claim 12 wherein
the sample fluid is water and the inert fluid is mercury.

14. The end cap of claim 12 wherein the end cap has a substantially flat planar surface for contacting the sample.

15. The end cap of claim 14 wherein variation in flatness of the end cap does not exceed 0.001 inch per inch.

16. The end cap of claim 12 including a groove in an apex thereof for receiving a portion of an impermeable jacket to be applied on the sample.

17. An end cap for disposition at an end of a rock sample to be tested in a triaxial test apparatus, the sample containing water, the end cap comprising, a body having a top and a bottom, a pore pressure channel in the body in fluid communication with the top of the body and into which water expelled from the sample during testing can flow, a pore pressure chamber in the body in fluid communication with the pore pressure channel, the pore pressure chamber fillable with mercury, a pore pressure transducer disposed in the pore pressure chamber for reacting to and sensing changes in the amount of water expelled from the sample during testing, and wiring connected to the pore pressure transducer and extending therefrom and out of the body, the wiring connectible to a system for monitoring and recording changes sensed by the pore pressure transducer, the end cap having a substantially flat planar surface for contacting the sample whose variation in flatness does not exceed 0.001 inch per inch.

18. Triaxial test apparatus for testing rock samples in a housing fillable with confining fluid for providing confining pressure on a sample to be tested, the sample having a top and a bottom, the housing having a channel for introduction therein and removal therefrom of the confining fluid, the housing having an opening therethrough through which a portion of a load piston sealingly extends for providing a load on the sample, the triaxial test apparatus comprising sample mounting means for mounting the sample within the housing, the sample mounting means including a top end cap for mounting at the top of the sample and a bottom end cap for disposition at the bottom of the sample, the bottom end cap having a body and a pore pressure channel in the body in fluid communication with the bottom of the sample and into which flows sample fluid expelled from the sample during testing, the sample fluid contacting an inert fluid in the pore pressure channel, a pore pressure chamber in fluid communication with the pore pressure channel, the pore pressure chamber for containing an amount of the inert fluid, the pore pressure chamber disposed outside the housing and in fluid communication with the pore pressure channel of the bottom end cap through a stiff conduit disposed therebetween, a pore pressure transducer disposed in the pore pressure chamber for reacting to and sensing changes in the amount of sample fluid expelled from the sample during testing, wiring connected to the pore pressure transducer and extending therefrom the wiring connectible to a system for monitoring and recording changes sensed by the pore pressure transducer, the pore pressure channel and the pore pressure chamber filled with the inert fluid, the inert fluid immiscible with the sample fluid, at least one flexible impermeable jacket for enclosing the surface of the sample other than its ends and preventing the confining fluid from directly contacting the sample and preventing sample fluid from being expelled from the portion of the sample covered by the jacket, and the bottom end cap suitable for mounting on a load cell mounted within the housing.

19. The triaxial test apparatus of claim 18 wherein the sample fluid is water and the inert fluid is mercury.

20. A test method for triaxially testing a rock sample, the rock sample prepared by mounting it on a bottom end cap of a triaxial test apparatus, the end cap having a pore pressure channel extending therethrough for disposition contactingly adjacent the rock sample to be tested, the pore pressure channel for receiving sample fluid expelled from the sample during testing, a pore pressure chamber in fluid communication with the pore pressure channel through a stiff conduit connected therebetween, the pore pressure chamber having a pore pressure transducer mounted therein for reacting to and indicating changes in pressure of fluid in the chamber, evacuating substantially all the air from the pore pressure channel, the stiff conduit, and from the pore pressure chamber and then filling them with an inert fluid immiscible with the sample fluid, and in a sealed chamber, applying a flexible impermeable jacket to the sample, other than to its ends, and applying the bottom end cap to the bottom end of the sample and a top end cap to the top end of the sample, the sample having a pore pressure, the test method comprising placing the sample in a confinement vessel of a triaxial test apparatus and sealing the vessel shut, isostatically loading the sample by introducing a confining fluid under pressure into the confinement vessel to provide a constant confining pressure on the sample, allowing the sample's pore pressure to equilibrate with the pressure of the confining fluid, applying a load piston to the top end cap to apply a known load on the sample, the piston sealingly extending through the confinement vessel to contact the sample, and measuring and recording pore pressure of the sample continuously during the test.

21. Apparatus for measuring pore pressure of a low permeability geologic material, the apparatus comprising a body suitable for disposition in contact with a face of a sample of the geologic material, a pore pressure channel in and through the body, the channel situated for receiving sample fluid expelled from the sample when pressure is applied to the sample, the pore pressure channel filled with a pore pressure fluid which is inert, not miscible with the sample fluid, and in contact with the sample fluid, and in contact with the sample fluid when pressure is applied to the sample, a pore pressure transducer disposed in the pore pressure channel for reacting to and sensing changes in the pressure fluid in the pore pressure channel, and wiring connected to the pore pressure transducer and extending therefrom, the wiring connectible to a system for monitoring and recording changes sensed by the pore pressure transducer.

22. The apparatus of claim 21 wherein the sample fluid is water and the inert fluid is mercury.

23. The apparatus of claim 21 wherein substantially all air is evacuated from the pore pressure channel.

24. The apparatus of claim 21 including also indicating means in contact with the sample for indicating a change in a dimension of the sample, the indicating means having wiring connected thereto and connectible to a monitor/control system.

25. The apparatus of claim 21 wherein the geologic material is shale.

26. A method measuring pore pressure of a low permeability geologic material, the method comprising placing a face of sample of the geologic material in contact with a body having a pore pressure channel therethrough, the channel situated for receiving sample fluid expelled from the sample, applying pressure to the sample so that sample fluid is expelled therefrom and into the pore pressure channel, the sample fluid contacting an inert fluid which fills the pore pressure channel, the inert fluid not miscible with the sample fluid, sensing a change in pressure in the pore pressure fluid due to expelling of the sample fluid from the sample with a pore pressure transducer in the pore pressure channel, and transmitting a signal from the pore pressure transducer indicative of the change in pressure to a monitoring system that records such signals.

27. The method of claim 26 wherein the geologic material is shale.

28. The method of claim 26 wherein substantially all air is evacuated from the pore pressure channel.

29. The method of claim 26 wherein the sample fluid is water and the inert fluid is mercury.

* * * * *